US009675359B2

(12) United States Patent
Williams

(10) Patent No.: US 9,675,359 B2
(45) Date of Patent: Jun. 13, 2017

(54) SURGICAL INSTRUMENT WITH PRELOAD ASSEMBLY

(71) Applicant: Covidien LP, Mansfield, MA (US)

(72) Inventor: Justin Williams, Naugatuck, CT (US)

(73) Assignee: COVIDIEN LP, Mansfield, MA (US)

( * ) Notice: Subject to any disclaimer, the term of this patent is extended or adjusted under 35 U.S.C. 154(b) by 563 days.

(21) Appl. No.: 13/648,692

(22) Filed: Oct. 10, 2012

(65) Prior Publication Data

US 2014/0097226 A1  Apr. 10, 2014

(51) Int. Cl.
| | | |
|---|---|---|
| A61B 17/068 | (2006.01) | |
| A61B 17/115 | (2006.01) | |
| A61B 17/072 | (2006.01) | |
| A61B 17/00 | (2006.01) | |
| A61B 90/00 | (2016.01) | |

(52) U.S. Cl.
CPC ......... *A61B 17/1155* (2013.01); *A61B 17/068* (2013.01); *A61B 17/072* (2013.01); *A61B 17/07207* (2013.01); *A61B 17/115* (2013.01); *A61B 2017/00473* (2013.01); *A61B 2017/00991* (2013.01); *A61B 2090/034* (2016.02); *A61B 2090/0811* (2016.02)

(58) Field of Classification Search
CPC ............ A61B 17/07207; A61B 17/068; A61B 17/072; A61B 17/1155; A61B 2019/4857; A61B 17/115; A61B 2017/00473
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A * | 12/1981 | Conta ................. | A61B 17/115 227/179.1 |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

European Search Report EP 13 18 7923 dated Jan. 8, 2014.

(Continued)

*Primary Examiner* — Hemant M Desai
*Assistant Examiner* — Mobeen Ahmed

(57) ABSTRACT

A surgical instrument comprising a handle assembly, an elongated body portion extending distally from the handle assembly, a head portion and a preload assembly is disclosed. The head portion is disposed adjacent a distal end of the elongated body portion and includes an anvil assembly and a shell assembly. The anvil assembly is movable in relation to the shell assembly between spaced and approximated positions. The preload assembly is disposed in mechanical cooperation with the shell assembly and enables longitudinal movement of the shell assembly with respect to the elongated body portion.

1 Claim, 5 Drawing Sheets

(56) References Cited

U.S. PATENT DOCUMENTS

| | | | |
|---|---|---|---|
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,475,679 A * | 10/1984 | Fleury, Jr. | A61B 17/072 206/339 |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,665,917 A | 5/1987 | Clanton et al. | |
| 4,667,673 A | 5/1987 | Li | |
| 4,671,445 A * | 6/1987 | Barker | A61B 17/072 227/141 |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A * | 7/1988 | Barker | A61B 17/072 227/19 |
| 4,776,506 A * | 10/1988 | Green | A61B 17/115 227/19 |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A * | 4/1990 | Green | A61B 17/115 227/179.1 |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A * | 12/1993 | Grant | A61B 17/115 227/179.1 |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Bianco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A * | 11/1998 | Sauer | A61B 17/115 227/153 |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,916,146 A | 6/1999 | Allotta | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 * | 7/2001 | Balazs | A61B 17/115 227/175.1 |
| 6,264,086 B1 | 7/2001 | McGuckin, Jr. | |
| 6,269,997 B1 | 8/2001 | Balázs et al. | |

(56) References Cited

U.S. PATENT DOCUMENTS

| | | | |
|---|---|---|---|
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 * | 8/2004 | Orban, III ......... A61B 17/0644 227/176.1 |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 * | 9/2005 | Gresham ............. A61B 17/115 227/175.1 |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |

(56) References Cited

U.S. PATENT DOCUMENTS

| | | | |
|---|---|---|---|
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,181,838 B2 * | 5/2012 | Milliman ............ A61B 1/31 227/175.1 |
| 8,231,042 B2 * | 7/2012 | Hessler ............ A61B 17/1114 227/175.1 |
| 2003/0111507 A1 | 6/2003 | Nunez |
| 2004/0195289 A1 * | 10/2004 | Aranyi ............ A61B 17/072 227/180.1 |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2006/0273135 A1 * | 12/2006 | Beetel ............ A61B 17/068 227/175.1 |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0272722 A1 | 11/2007 | Aranyi |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 * | 1/2011 | Kostrzewski ........ A61B 17/115 227/176.1 |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0228358 A1 | 9/2012 | Zemlok |
| 2012/0273545 A1 * | 11/2012 | Mozdzierz ........ A61B 17/1155 227/175.1 |
| 2014/0224856 A1 * | 8/2014 | Smith ............ A61B 17/07207 227/175.1 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| WO | WO 8706448 A | 11/1987 |
| WO | WO 8900406 A1 | 1/1989 |
| WO | WO 9006085 A1 | 6/1990 |

OTHER PUBLICATIONS

Extended European Search Report corresponding to EP 14 18 8317.3, completed Feb. 4, 2015 and dated Feb. 12, 2015; (6 pp).
European Office Action corresponding to counterpart Int'l Appln No. EP 14 188 317.3 dated Nov. 4, 2015.
Extended European Search Report corresponding to counterpart Int'l Appln No. EP 15 17 9895.6 dated Dec. 3, 2015.

(56) References Cited

OTHER PUBLICATIONS

Chinese First Office Action corresponding to counterpart Int'l Appln. No. CN 2013104714311 dated Dec. 2, 2016.
European Office Action corresponding to counterpart Int'l Appln. No. EP 14 18 8317.3 dated Oct. 28, 2016.

* cited by examiner

SURGICAL INSTRUMENT WITH PRELOAD ASSEMBLY

BACKGROUND

Technical Field

The present disclosure relates generally to a surgical instrument for applying surgical fasteners to body tissue. More particularly, the present disclosure relates to a surgical instrument suitable for performing circular anastomosis and/or treatment to internal walls of hollow tissue organs.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Besides anastomosis of hollow organs, surgical instruments for performing circular anastomosis have been used to treat internal hemorrhoids in the rectum. Typically, during use of a circular stapling instrument for hemorrhoid treatment, the anvil head and the staple holding component of the surgical instrument are inserted through the anus and into the rectum with the anvil head and the staple holding component in an open or unapproximated position. Thereafter, a purse-string suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue and staple the cut tissue.

SUMMARY

The present disclosure relates to a surgical instrument comprising a handle assembly, an elongated body portion extending distally from the handle assembly, a head portion and a preload assembly. The head portion is disposed adjacent a distal end of the elongated body portion and includes an anvil assembly and a shell assembly. The anvil assembly is movable in relation to the shell assembly between spaced and approximated positions. The preload assembly is disposed in mechanical cooperation with the shell assembly and enables longitudinal movement of the shell assembly with respect to the elongated body portion.

In disclosed embodiments, the preload assembly includes a biasing member coaxially disposed about a portion of the elongated body portion.

In disclosed embodiments, the preload assembly biases the shell assembly toward the anvil assembly.

In disclosed embodiments, the preload assembly enables proximal and distal longitudinal movement of the shell assembly with respect to the elongated body portion.

In disclosed embodiments, the preload assembly includes an outer tube disposed concentrically around the elongated body portion and in mechanical cooperation with the shell assembly, and where the outer tube is longitudinally translatable with respect to the elongated body portion. Here, it is envisioned that the preload assembly includes a biasing element disposed in contact with a proximal portion of the outer tube. Here, it is envisioned that the preload assembly includes a housing disposed around the biasing element and around a proximal portion of the outer tube. Here, it is further envisioned that the preload assembly includes a retainer disposed in mechanical cooperation with the housing and which is configured to limit the distal travel of the outer tube by preventing a proximal lip of the outer tube from being translated distally therepast. It is further envisioned that the housing of the preload assembly is disposed in contact with the handle assembly.

The present disclosure also relates to a preload assembly for use with a surgical instrument including an elongated body portion and an anvil assembly that is longitudinally movable toward a shell assembly. The preload assembly comprises an outer tube disposed in mechanical cooperation with the shell assembly, and a biasing member disposed in mechanical cooperation with the outer tube and configured to distally bias the outer tube toward the anvil assembly.

In disclosed embodiments, the biasing member enables proximal and distal longitudinal movement of the shell assembly with respect to the elongated body portion.

In disclosed embodiments, the outer tube is longitudinally translatable with respect to the elongated body portion of the surgical instrument.

In disclosed embodiments, the biasing element is disposed in contact with a proximal portion of the outer tube.

In disclosed embodiments, the preload assembly further comprises a housing disposed around the biasing element and around a proximal portion of the outer tube. Here, it is envisioned that the preload assembly further comprises a retainer disposed in mechanical cooperation with the housing. The retainer is configured to limit the distal travel of the outer tube by preventing a proximal lip of the outer tube from being translated distally therepast.

The present disclosure also relates to a method of performing a surgical procedure. The method comprises providing a surgical instrument including a handle assembly, an elongated body portion extending distally from the handle assembly and defining a longitudinal axis, a head portion disposed adjacent a distal end of the elongated body portion and including an anvil assembly and a shell assembly, and a preload assembly. The preload assembly is disposed in mechanical cooperation with the shell assembly and enables longitudinal movement of the shell assembly with respect to the elongated body portion. The method also includes positioning the surgical instrument adjacent a surgical site, moving the anvil assembly towards its approximated position, and ejecting fasteners from the shell assembly toward the anvil assembly.

In disclosed embodiments, the preload assembly enables proximal and distal longitudinal movement of the shell assembly with respect to the elongated body portion.

In disclosed embodiments, the preload assembly includes an outer tube disposed concentrically around the elongated body portion and in mechanical cooperation with the shell assembly. The outer tube is longitudinally translatable with respect to the elongated body portion. Here, it is envisioned that the preload assembly includes a biasing element disposed in contact with a proximal portion of the outer tube. It is further envisioned that the preload assembly includes a housing disposed around the biasing element and around a proximal portion of the outer tube.

DESCRIPTION OF THE DRAWINGS

Various embodiments of the presently disclosed surgical instrument are disclosed herein with reference to the drawings, wherein.

DETAILED DESCRIPTION OF EMBODIMENTS

Figure 1:
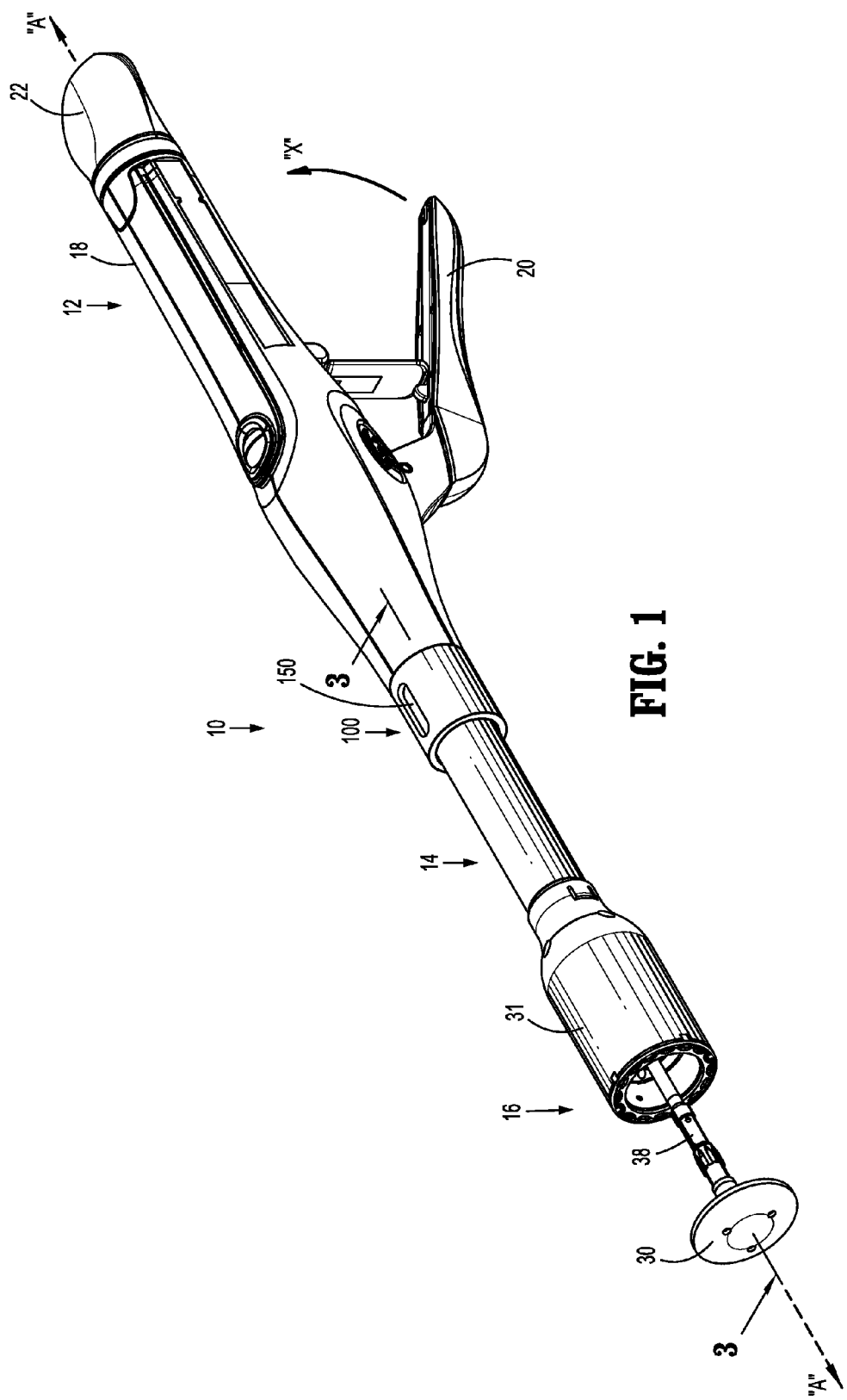
FIG. 1 is a perspective view of the presently disclosed surgical instrument illustrated in an open position, in accordance with an embodiment of the present disclosure.

Embodiments of the presently disclosed surgical instrument and preload assembly will now be described in detail with reference to the drawings in which like reference numerals designate identical or corresponding elements in each of the several views. Throughout this description, the term "proximal" will refer to the portion of the instrument closer to the operator and the term "distal" will refer to the portion of the instrument farther from the operator.

FIG. 1 illustrates the presently disclosed surgical instrument shown generally as 10. Briefly, surgical instrument 10 includes a handle assembly 12, an elongated body portion 14, and a head portion 16. Elongated body portion 14 defines a longitudinal axis "A." Additionally, while not explicitly shown, the present disclosure also contemplates a curved elongated body portion. The length, shape and/or the diameter of elongated body portion 14 and head portion 16 may also be varied to suit a particular surgical procedure.

With continued reference to FIG. 1, handle assembly 12 includes a stationary handle 18, a movable handle 20, a rotatable approximation knob 22 and a preload assembly 100. Head portion 16 includes an anvil assembly 30 and a shell assembly 31. Anvil assembly 30 is movable in relation to shell assembly 31 between spaced and approximated positions by rotation of approximation knob 22. Preload assembly 100 biases shell assembly 31 distally toward anvil assembly 30. Further details of preload assembly 100 are discussed below.

Figure 5:
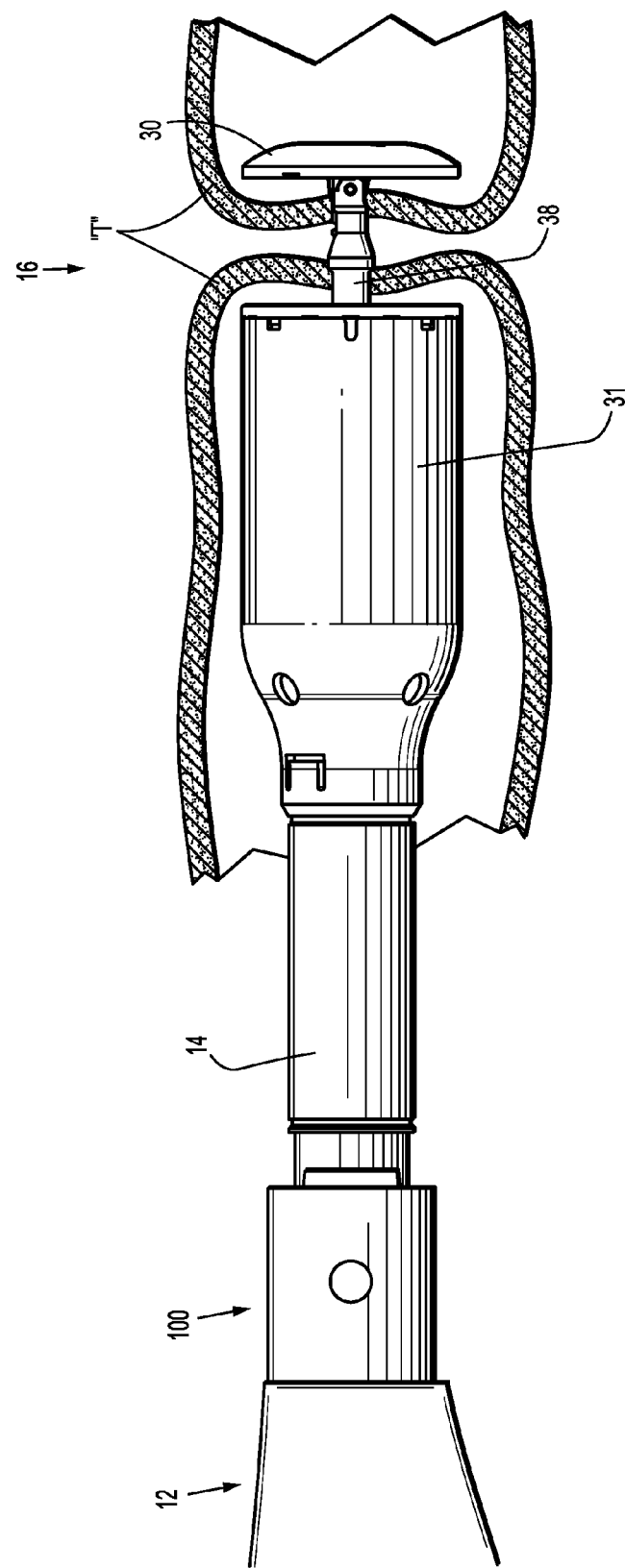
FIG. 5 is a side view of a distal portion of the surgical instrument of FIG. 1 shown in an open position within tissue.
Figure 6:
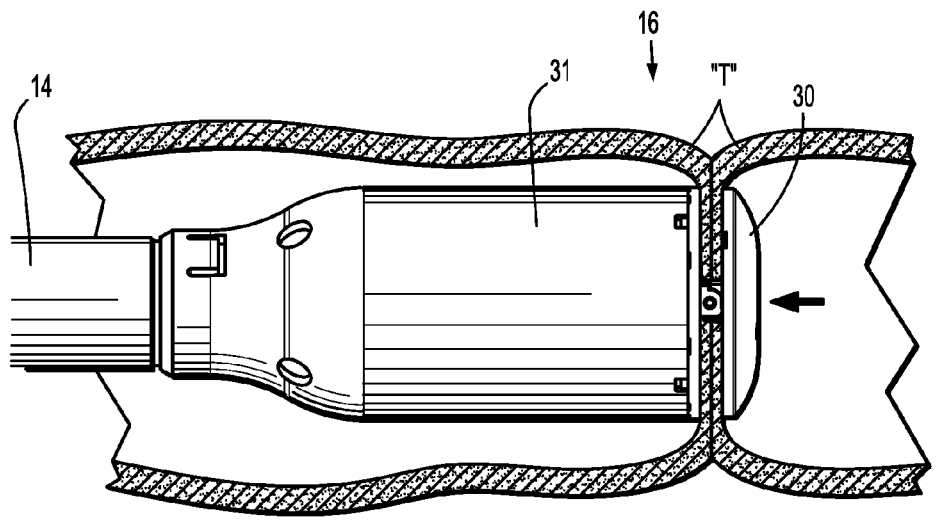
FIG. 6 is a side view of a distal portion of the surgical instrument of FIG. 1 shown in an approximated position within tissue.

In operation, rotation of approximation knob 22 causes movement of anvil assembly 30 in relation to shell assembly 31 between a spaced position (FIGS. 1 and 5) and an approximated position (FIG. 6), as approximation knob 22 is mechanically engaged with an anvil retainer 38 (FIG. 1), which is fastened to anvil assembly 30. It is envisioned that rotation of approximation knob 22 in a first direction (e.g., clockwise) causes proximal movement of anvil assembly 30, and rotation of approximation knob 22 in a second opposite direction (i.e., counter-clockwise) causes distal movement of anvil assembly 30. Further details of the operation of approximation knob 22 are described in U.S. Pat. No. 8,113,403, which was filed on Aug. 25, 2009, the entire contents of which being incorporated by reference herein.

With reference to FIGS. 2-7, further details of preload assembly 100 are illustrated. As shown, preload assembly 100 includes a biasing element 110, a housing 120, an outer tube 130, and a retainer 140. Housing 120 is disposed coaxially around a proximal portion of elongated body portion 14 and extends distally from handle assembly 12. It is envisioned that housing 120 is in contact with handle assembly 12 and is fixed from longitudinal movement with respect to handle assembly 12. It is further envisioned that housing 120 is integrally formed with handle assembly 12. Biasing element 110 (e.g., a compression spring, parallel wave spring, etc.) is coaxially positioned around elongated body portion 14 and is positioned within housing 120.

Outer tube 130 extends distally from housing 120 toward shell assembly 31. More particularly, a proximal portion 132 of outer tube 130 is slidably disposed within housing 120 of preload assembly 100 and about elongated body portion 14; a distal portion 134 of outer tube 130 is affixed to shell assembly 31. Further, proximal portion 132 includes a lip 136 extending radially outward (i.e., away from the longitudinal axis "A").

Figure 2:
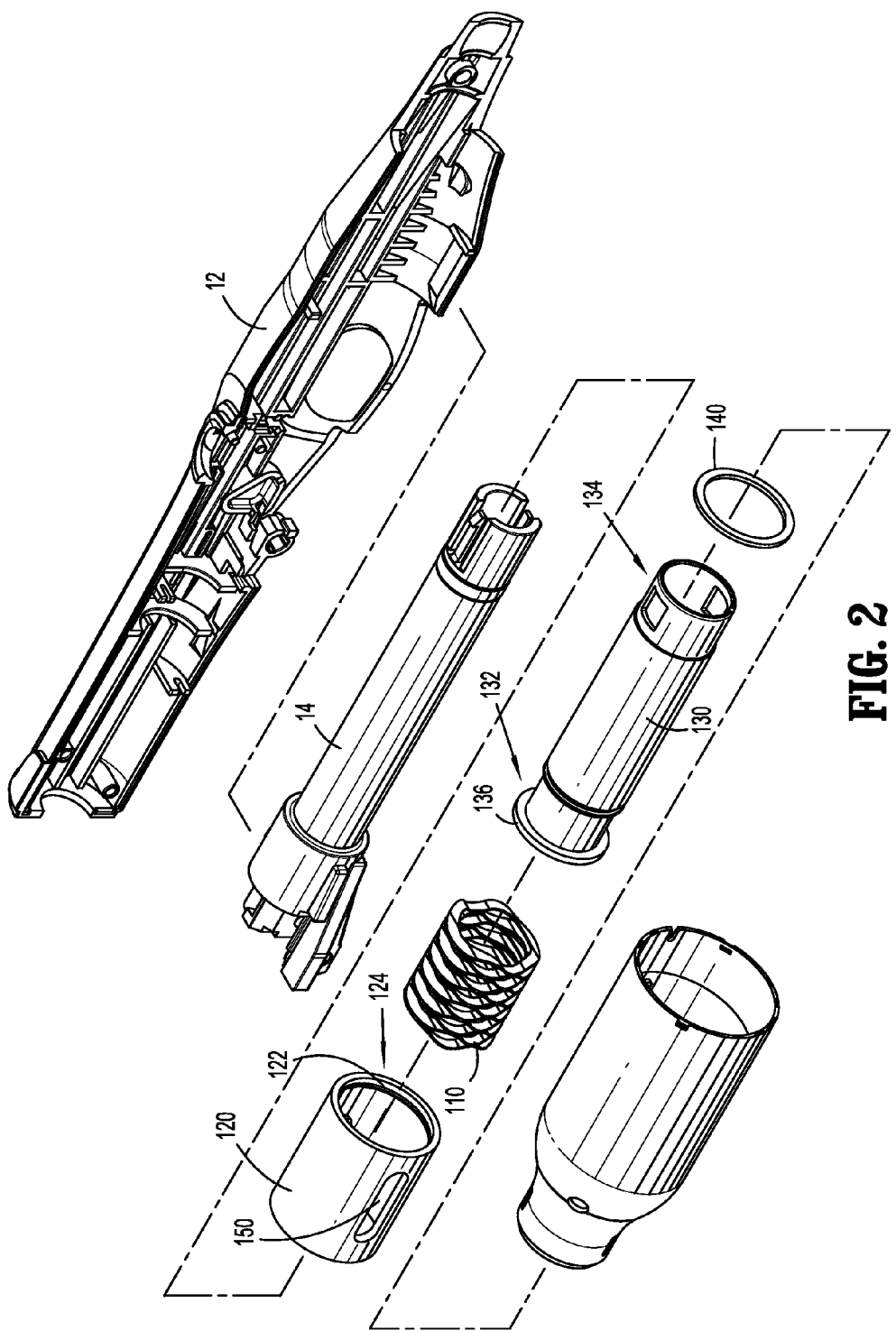
FIG. 2 is a perspective, assembly view of a portion of the surgical instrument of FIG. 1.
Figure 3:
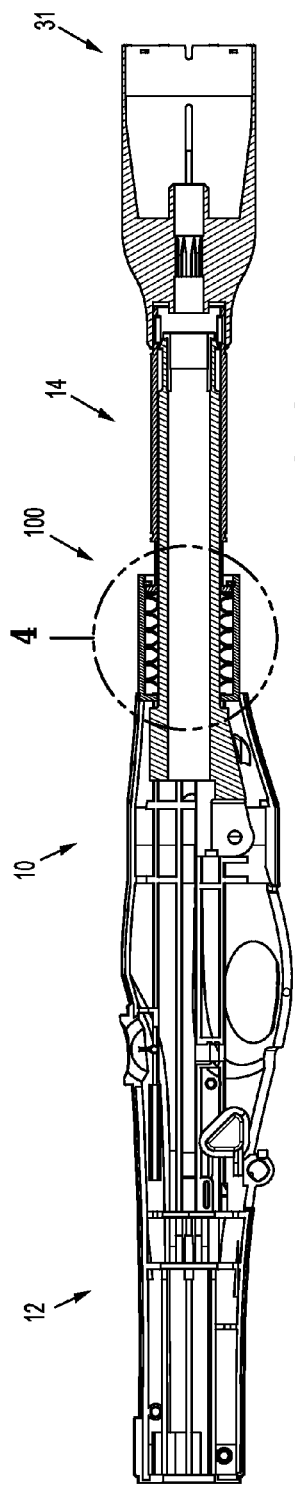
FIG. 3 is a longitudinal cross-sectional view taken along line 3-3 of FIG. 1, with some parts omitted.
Figure 4:
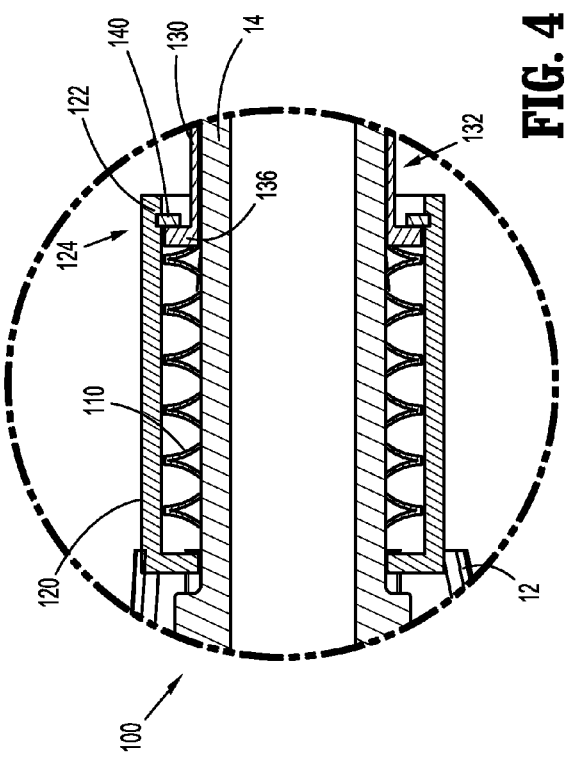
FIG. 4 is an enlarged portion of the area of detail indicated in FIG. 3.
Figure 7:
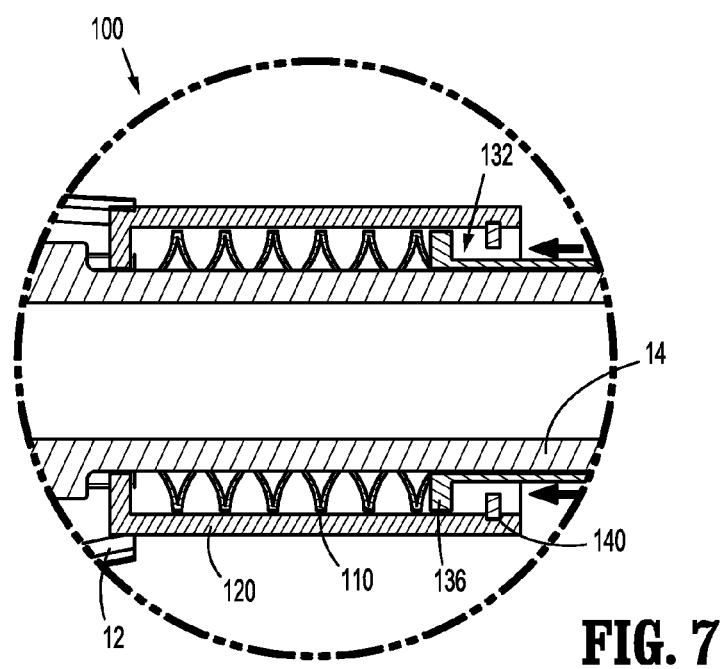
FIG. 7 is a longitudinal cross-sectional view of an enlarged portion of the surgical instrument of FIG. 1 shown in an approximated position.

With reference to FIGS. 2, 4, and 7, retainer 140 is positioned in mechanical cooperation with housing 120 and extends radially inward therefrom. Specifically, it is envisioned that retainer 140 is positionable within a slot 122 located in a distal portion 124 of housing. With particular reference to FIG. 4, retainer 140, and in particular, the engagement between retainer 140 and lip 136, prevents outer tube 130 from moving distally beyond and out of housing 120.

Accordingly, as can be appreciated, biasing element 110 of preload assembly 100 provides a distally biasing force which distally biases outer tube 130, and thus distally biases shell assembly 31 toward anvil assembly 30. Additionally, as discussed below, preload assembly 100 allows proximal movement of shell assembly 31 with respect to elongated body portion 14.

In use, when head portion 16 is in the open, unclamped position (FIG. 5), preload assembly 100 distally biases shell assembly 31 toward anvil assembly, and toward tissue "T." As can be appreciated, the spring constant of the biasing element 110 can be preselected (prior to assembly of preload assembly 100) to provide the optimum clamping pressure for a particular procedure. The distal pressure exerted against shell assembly 31 by preload assembly 100 helps prevent "under clamping." "Under clamping" may otherwise occur when anvil assembly 30 is not approximated a sufficient amount and/or when anvil assembly 30 and shell assembly 31 relatively move toward the open position in response to attempting to clamp tissue that is too thick or in response to the force created when firing fasteners from shell assembly 31 toward anvil assembly 30. In surgical devices that clamp up to a set distance between the anvil and cartridge assembly, over clamping or under clamping, in which the clamping forces are too high or too low, can occur. The preloaded spring or other biasing device in the preload assembly applies a preselected clamping force. An indicator can be provided, in any of the embodiments disclosed herein, to show the movement of the shell, thereby indicating whether the reload selected is optimal for the tissue thickness. The biasing device can be a parallel wave spring, coil spring, bevel spring, or any other kind of spring.

Additionally, as shown in FIG. 7, preload assembly 100 allows outer tube 130 (and thus shell assembly 31) to move proximally with respect to elongated body portion 14. Proximal movement of shell assembly 31 and outer tube 130 occurs when head assembly 16 is in the approximated position and when the clamping pressure exerted by approximation knob 22 causes the tissue "T" between anvil assembly 30 and shell assembly 31 to compress. Compression of tissue "T" can also result during the ejection of fasteners from shell assembly 31 toward anvil assembly 30. The amount of tissue compression that occurs (i.e., along longitudinal axis "A") corresponds to the amount of proximal translation of outer tube 130 against the bias of biasing element 110.

The proximal movement of shell assembly 31 with respect to elongated body portion 14, which is enabled by preload assembly 100, helps prevent "over clamping." "Over clamping" may otherwise occur when anvil assembly 30 and shell assembly 31 are fully approximated, and an additional clamping force is provided (e.g., by continued actuation of approximation knob 22). Preload assembly 100 helps prevent "over clamping" by allowing shell assembly 31 to move away from anvil assembly 30 (i.e., proximally) in situations where anvil assembly 30 and shell assembly 31 are fully approximated and an additional clamping force is provided. Thus, preload assembly 100 helps prevent "under clamping" and "over clamping."

Once head assembly 16 is sufficiently approximated, actuation of movable handle 20 (i.e., pivoting in the direction of arrow "X" in FIG. 1), causes fasteners to be ejected from shell assembly 31 toward anvil assembly 30. That is, movable handle 20 is disposed in mechanical cooperation with a pusher (not explicitly shown in the illustrated embodiments), such that actuation of movable handle 20 causes advancement of the pusher into contact with the fasteners, which ejects into staple deforming pockets of anvil assembly 30.

The present disclosure also contemplates a tissue indicator 150 (see FIGS. 1 and 2). Tissue indicator 150 includes a window on housing 120 which allows a user to see lip 136 of outer tube 130, and its amount of travel (e.g., during approximation of head assembly 16). Tissue indicator 150 may include indicia (e.g., measurement lines and associated numbers) to further facilitate determining the thickness, type, or amount of tissue being clamped or compressed. This information may be effective to help the user determine the optimal staple size for the desired procedure.

Further details of other features of surgical instrument 10, such as the approximation assembly, firing assembly, lock out mechanism and an additional indicator mechanism are disclosed in commonly-owned U.S. Pat. Nos. 7,168,604, 7,303,106, and 8,113,403, the entire contents of each of which are incorporated by reference herein.

The present disclosure also relates to a method of performing a surgical procedure. The method includes providing a surgical instrument 10 including a handle assembly 12, an elongated body portion 14 extending distally form handle assembly 12, a head portion 16 and a preload assembly 100. Handle assembly 12 includes a stationary handle 18 and a movable handle 20, which is movable between a first non-actuated position and a second actuated position. Head portion 16 is disposed adjacent a distal end of the elongated body portion 14 and includes an anvil assembly 30 and a shell assembly 31. Anvil assembly 30 is movable in relation to shell assembly 31 between spaced and approximated positions. The method also includes positioning surgical instrument 10 adjacent a surgical site, moving anvil assembly 30 toward its approximated position, and moving movable handle 20 through a firing stroke to eject fasteners from shell assembly 31 toward anvil assembly 30.

It is also contemplated that the apparatus has a replaceable head including the cartridge assembly, anvil assembly and associated mechanisms. The stapling instrument 10 can include the manually actuated handle assembly of FIG. 1 and as described above, or can include a powered actuator assembly having first and second drive members. For example, U.S. patent application Ser. No. 12/946,082, filed Nov. 15, 2010, the entire disclosure of which is hereby incorporated by reference herein, discloses a surgical device having a powered actuator assembly. Such actuator assembly can be powered by a motorized handle.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

The invention claimed is:

1. A surgical instrument, comprising:
a handle assembly;
an elongated body portion extending distally from the handle assembly and defining a longitudinal axis;
a head portion disposed adjacent and in contact with a distal end of the elongated body portion and including an anvil assembly and a shell assembly, the anvil assembly being movable in relation to the shell assembly between spaced and approximated positions, wherein when the anvil assembly moves toward the approximated position, the anvil assembly moves in a proximal direction with respect to the elongated body portion; and
a preload assembly disposed in mechanical cooperation with the shell assembly, the preload assembly enabling longitudinal movement of the shell assembly with respect to the elongated body portion, the preload assembly including a housing, an outer tube, and a biasing member, the biasing member being disposed concentrically around the elongated body portion, a majority of the outer tube is disposed concentrically around the elongated body portion and in mechanical cooperation with the shell assembly, the outer tube being longitudinally translatable with respect to the elongated body portion, the biasing member being disposed in contact with a proximal portion of the outer tube and biases the outer tube distally with respect to the elongated body portion, the housing being disposed concentrically around the biasing member and concentrically around the proximal portion of the outer tube, and wherein the housing is disposed in contact with the handle assembly.

* * * * *